United States Patent [19]

Dingeman et al.

[11] Patent Number: 4,888,005

[45] Date of Patent: Dec. 19, 1989

[54] CATHETER TUBE CARRYING DEVICE AND METHOD

[75] Inventors: David L. Dingeman, Duluth; Christine E. Hendrickson, Minnetonka, both of Minn.

[73] Assignee: Cathex Tray Corporation, Duluth, Minn.

[21] Appl. No.: 144,259

[22] Filed: Jan. 15, 1988

[51] Int. Cl.[4] .......... A61M 1/00; A61M 5/32

[52] U.S. Cl. .......... 604/326; 280/304.1; 297/188; 297/DIG. 4; 604/174

[58] Field of Search .......... 224/42.43; 280/289 WC, 280/242 WC, 657; 297/188, 192, 193, DIG. 4; 604/174, 178, 322, 326

[56] References Cited

U.S. PATENT DOCUMENTS

| | | | |
|---|---|---|---|
| 3,081,464 | 3/1963 | Lochner | 5/92 |
| 3,090,968 | 5/1963 | Buono | 4/110 |
| 3,345,023 | 10/1967 | Scott et al. | 248/95 |
| 3,666,131 | 5/1972 | Thompson | 214/621 |
| 3,896,809 | 7/1975 | Samuel et al. | 297/188 |
| 4,101,991 | 7/1978 | Sandonato | 5/90 |
| 4,146,265 | 3/1979 | Ocel et al. . | |
| 4,179,159 | 12/1979 | Sieklucki et al. | 297/192 |
| 4,264,085 | 4/1981 | Volin | 280/289 |
| 4,308,642 | 1/1982 | Heyman | 24/306 |
| 4,403,786 | 9/1983 | Ulics | 280/289 |
| 4,491,257 | 1/1985 | Ingles | 224/42.45 R |
| 4,553,770 | 11/1985 | Lyman | 280/289 |
| 4,592,570 | 6/1986 | Nassiri | 280/650 |
| 4,593,929 | 6/1986 | Williams | 280/650 |
| 4,600,209 | 7/1986 | Kerr, Jr. | 280/400 |
| 4,613,994 | 9/1986 | Oates | 4/480 |
| 4,648,615 | 3/1987 | Volin | 280/242 |
| 4,718,689 | 1/1988 | Lott | 604/326 |

*Primary Examiner*—Jerome L. Kruter
*Attorney, Agent, or Firm*—Merchant, Gould, Smith, Edell, Welter & Schmidt

[57] ABSTRACT

A catheter tube carrying device for use in conjunction with the use of a wheelchair by a catheterized person. The carrying device includes catheter tube support means for engaging excess catheter tubing of a gravity flow drainage system for an catheter. The carrying device is used to maintain the gravity flow drainage system by supporting catheter tubing in a horizontal orientation when the catheter tube carrying device is engaged below the seat of the wheelchair. The carrying device preferably includes drainage bag support means for supporting the drainage bag at an elevation lower than the elevation of the drainage tube. Preferably, the carrying device is attached to cross-braces below the set of the wheelchair. Methods for maintaining the gravity flow drainage system are also provided.

15 Claims, 3 Drawing Sheets

FIG. 2
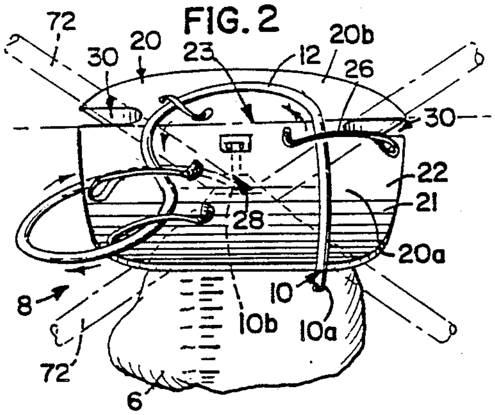
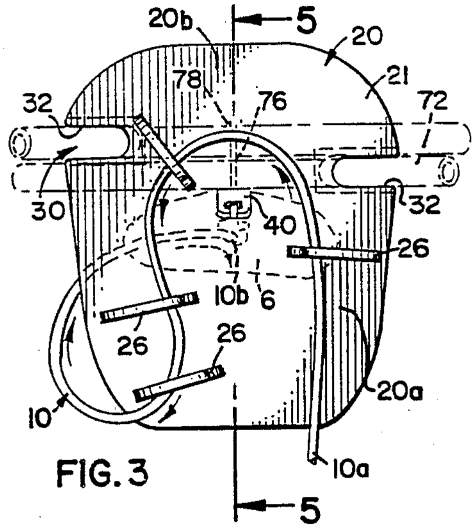
FIG. 3
FIG. 4
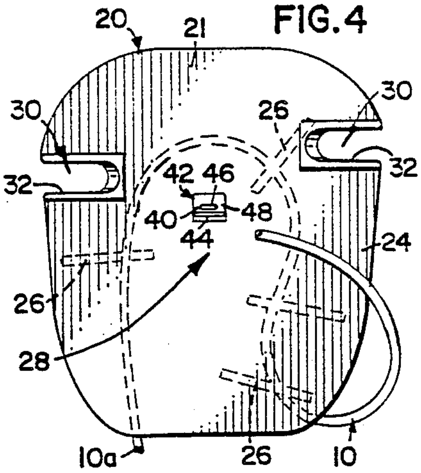
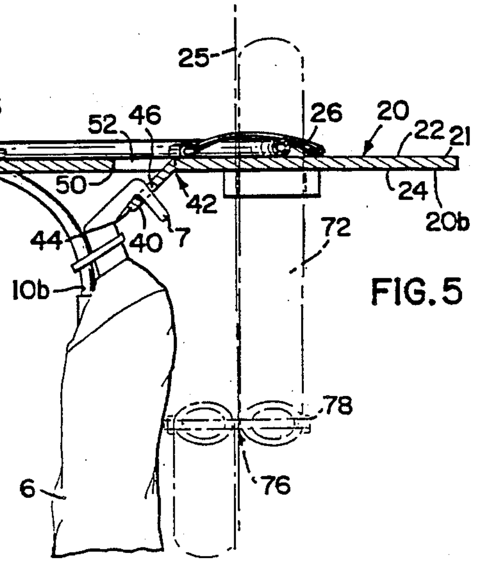
FIG. 5
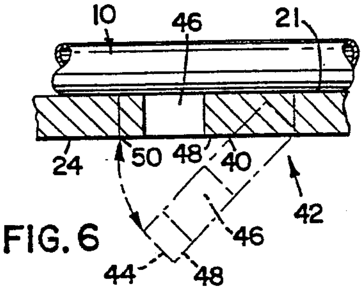
FIG. 6

FIG. 7
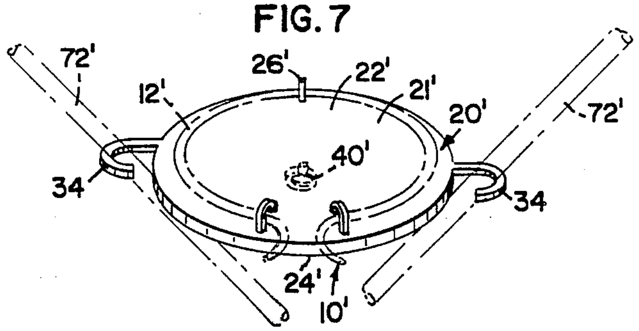
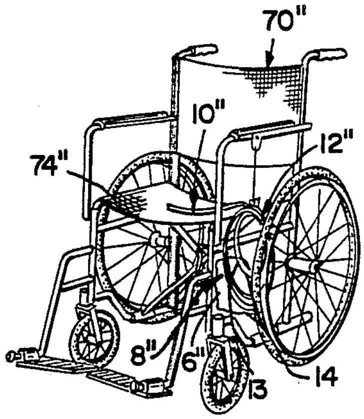
FIG. 8
PRIOR ART

CATHETER TUBE CARRYING DEVICE AND METHOD

FIELD OF THE INVENTION

This invention relates to a device for carrying excess catheter drainage tubing such that a gravity flow drainage system for indwelling urinary catheters may be maintained for catheters inserted into patients and residents, such as those in hospitals and residential nursing homes, who spend part of the day in a wheelchair and the rest of the day in bed. The invention also relates to methods for maintaining such a system.

BACKGROUND OF THE INVENTION

Many hospital patients and nursing home residents suffer from an inability to restrain natural urinary discharge. This condition, referred to as incontinence, is evidenced by the involuntary intermittent or continuous flow of urine from the bladder as a result of an ineffective sphincter muscle or muscles which normally closes the urethra. The sphincter muscles may be weak, as is often the case with older individuals, particularly bed patients, or they may have been torn or otherwise damaged. A common cause of sphincter muscle damage in women occurs during childbirth. The disorder also occurs after prostate gland surgery in men. The condition is sometimes referred to as "stress incontinence" because of the minimal stress, if any, required to void the bladder.

Patients or residents who suffer from incontinence are generally furnished with an indwelling urinary catheter equipped with a flexible catheter drainage tube which is connected to a urinary discharge or drainage bag which collects the urine as it is passed by the patient or resident. The indwelling catheter is inserted directly into the urethra or the bladder and must be maintained in this position for many of these incontinent patients or residents for days at a time. A preferred catheter, referred to as a "Foley" catheter, is inserted directly into the bladder through the urethra. Once the tip of the "Foley" catheter is in the bladder, water or air is used to inflate the tip of the catheter so that the inflated tip does not slip back out of the bladder through the urethra which is much smaller than the now inflated catheter tip.

Unfortunately, the indwelling urinary catheter, especially "Foley" catheters, can cause bacterial infection in the patient's or the resident's urethra or bladder when the catheter drainage tube is allowed to become contaminated with bacteria. Serious infection may result if it is not recognized and treated promptly, thereby resulting in cases of septic shock where the infection goes untreated for a period of time. This condition is life threatening, especially for older individuals who have a reduced capacity to fight off such infections. The Applicants have observed that 85–90% of the patients/residents they have observed with septic shock in hospitals and nursing homes, developed this condition as a result of a bladder infection. In addition, about 85–90% of those patients/residents had an indwelling "Foley" catheter inserted into the bladder and connected to a gravity flow drainage system. It is believed that such an infection is often a result of a failure of the gravity flow drainage system to drain properly, thereby allowing urine to collect in vertical loops or low areas in the drainage tube. The stagnant urine provides a medium for exponential growth of infectious bacteria. When additional urine is passed by the patient/resident and stagnant urine has collected and bacteria have multiplied in low points in the drainage tube, the newly passed urine can mix with the stagnant urine and back up into the urethra and/or the bladder, thereby causing infection which can result in acute septic shock. Furthermore, when stagnant urine collects in low points in the drainage tube which are closer to the catheter than the to the drainage bag, there is a greater chance that bacteria could "creep" or grow along the inside wall of the tube, reaching the catheter and infecting the bladder and/or urethra, when the distance to traverse is less than it would otherwise be. Some manufacturers have inserted check valves in the urine tube in an attempt to prevent backflow of urine but infections continue to occur.

This problem can occur because the flexible urinary catheter drainage tube attached to the indwelling catheter generally has a length which is adapted to provide a gravity flow drainage system for a patient or resident who is lying in a bed. When the patient is moved from a bed to a wheelchair, however, the drainage tubing is generally much longer than is needed to reach a drainage bag which is somehow attached to the wheelchair. Therefore, when the patient/resident is sitting in a wheelchair, the drainage tube has extra length which is not required. This excess drainage tubing is generally collected in such a way that the excess catheter tubing is allowed to loop in a manner which runs perpendicular to the floor. These vertical loops have low spots which are potential areas for collecting stagnant urine and for interrupting the gravity flow drainage system.

The drainage system generally used for indwelling catheters is based on the natural flow of the urine drawn by the force of gravity after it leaves the bladder through the indwelling catheter. If uninterrupted, the urine will flow from the catheter to the drainage bag via the catheter drainage tube. Once this system is interrupted, however, the chance for infection of the bladder is increased. The vertical loop or loops in the excess catheter tubing, often created when a patient/resident is moved from a bed into a wheelchair, allow for interruption of the gravity flow drainage system, because urine collects in low spots in these loops. This problem is especially significant for those patients or residents with low urinary outputs. In such cases, often resulting from renal failure or poor fluid intake, the urine collects and becomes stagnant in low spots in the vertical loops. This is because the quantity of urine passed by the individual patient or resident is not sufficient to push the urine through the low spots and past the adjacent elevated spots in the loops due to the force of gravity. When the urine collects in this way it interrupts the gravity flow drainage system and allows for a high possibility of exponential bacterial multiplication in the drainage tube at a point which is much closer to the bladder than the more removed drainage bag. Also, because of the gravity-induced interruption in the gravity flow drainage system caused by the effect of the vertical loop, which requires the urine to pass through a high point in the loop before it will leave the loop containing the low point, the urine may back up into the catheter after failing to pass through such a high point, thereby allowing for a further potential for contamination and infection.

Another serious problem is contamination of the external surface of the bag and tubing by contact with the floor or other unsanitary surfaces since bacteria may then travel along the external surface of the bag and tube and enter the bladder via the external surface of the catheter.

Other problems exist as well. Wheelchairs have no appropriate place to hang the drainage bag itself. If the bag is hung over or under the side arm board of the wheelchair, the drainage bag is placed at a level only inches above or below the level of the bladder which makes it very difficult to maintain a gravity flow drainage system. Another option for hanging the drainage bag is the junction between the crossbraces located below the seat of the wheelchair. Unfortunately this puts the drainage bag in close proximity with the floor, increasing the chance of cross-contamination and damage to the bag when the wheelchair is moved. Furthermore, the bag draws visual attention when it hangs so low below the wheelchair especially if it drags along the floor when the wheelchair is moved. This visual attention diminishes the privacy which patients/residents would otherwise have, and can be an embarrassment to them. Furthermore, attempts to hook the drainage bag to the cross-braces, which are generally about 1 inch in diameter, result in frequent disconnections resulting in the drainage bag ending up on the floor and being exposed to contamination because proper attachment means have not been made available with many of the drainage bags previously available. Some institutions have developed solutions including the use of home-made container devices, such as cloth purses, which are designed to contain the drainage bag. However, when the drainage bag sits in such a device, which may be hung below the side arm board, the excess catheter tubing still possesses vertical loops which are perpendicular to the floor, thereby causing interruptions in the gravity flow drainage system. The frequency of cleaning such cloth bags is a concern in maintaining sanitary conditions around the catheter tubing and the drainage bag.

One partial solution to this problem would be to switch the drainage tube when the patient/resident is switched from a bed to a wheelchair. However, even if a simple disconnect system could be designed, it would require opening the otherwise "closed" system, increasing the chance of bacterial entry into the closed system from the outside surface of the tubing, thus providing additional potential for contamination which could lead to infection. Furthermore, such a system would not be readily accepted by those who are required to do the extra work of switching tubes every time a patient is moved from the bed to the wheel-chair and vice versa.

It will be appreciated from the foregoing that there are many problems associated with the need for urinary catheterization which are in need of solutions. The present invention provides solutions for these and other problems which have not been discussed.

SUMMARY OF THE INVENTION

In accordance with the present invention a catheter tube carrying device is provided for use in conjunction with the use of a wheelchair by a person who must be catheterized, the wheelchair having a seat and cross-braces below the seat. The catheter tube carrying device comprises catheter tube engaging means for receiving catheter tubing of a gravity flow drainage system for a catheter. The gravity flow drainage system includes a flexible catheter drainage tube including catheter tubing and an indwelling urinary drainage bag. The drainage tube connects the catheter to the drainage bag so that fluid can pass from the catheter to the drainage bag through the tube. The catheter tubing is engageable in the catheter tube engaging means such that a portion of the catheter tubing can be retained in such a position that retained tubing provides a substantially horizontal or a descending pathway for fluid which passes through the catheter tubing to the drainage bag from the catheter. Preferably, the carrying device comprises drainage bag support means for supporting the drainage bag at an elevation lower than the elevation of the excess catheter tubing received by the catheter tube engaging means.

A preferred embodiment of the present invention provides a catheter tube carrying device for attachment to a wheelchair, the wheelchair having a seat. The catheter tube carrying device comprises a support member, the support member including wheelchair attaching means for attaching the support member to the wheelchair at an elevation lower than the elevation of the seat. The support member also includes catheter tube engaging means for receiving excess catheter tubing of a gravity flow drainage system for an indwelling urinary catheter. The gravity flow drainage system includes a flexible catheter drainage tube and a drainage bag. The drainage tube connects the catheter to the drainage bag such that fluid can pass from the catheter to the drainage bag through the tube. The excess catheter tubing is a portion of the flexible catheter drainage tube which is in excess of that required to span a distance of a direct, passable, decending pathway between the indwelling urinary catheter positioned appropriately in a urinary passageway of a person sitting in the seat of the wheelchair, and the drainage bag when the drainage bag is located at an elevation lower than the elevation of the seat of the wheelchair. The support member is attachable to the wheelchair such that excess catheter tubing received by the catheter tube engaging means is retained in a substantially horizontal orientation. Preferably, the support member includes drainage bag support means for supporting the drainage bag at an elevation lower than the elevation of the excess catheter tubing, while insuring that the bottom of the drainage bag does not touch or drag on the floor when the excess tubing is received by the catheter tube engaging means.

The attaching means preferably include cross-brace receiving means for receiving the cross-braces of a wheelchair having opposite cross-braces located below the seat and supporting the wheelchair. This makes it possible to attach the carrying device to the wheelchair by engaging the cross-braces in the cross-brace receiving means. Preferably, the cross-brace receiving means include slip fit recess means for engaging the cross-braces. The recess means include a plurality of slip fit recesses, each recess having inner surfaces which contact the cross-braces atleast two opposing locations thereby engaging the cross-braces in a torsion loaded fit. This allows attachment to a wide variety of wheelchair sizer since the device will slip down the cross-braces until it is securely attached. The torsion load is created by a weight imbalance between the front two-thirds of the device and the rear one-third of the device, such that the front two-thirds outweigh the rear one-third thereby creating a force urging the front two-thirds downward when the recesses, located substantially proximate the interface between the front two-thirds and the rear one-third, are engaged on the cross-braces.

The drainage bag support means preferably include a pop-down drainage bag support ring attached to the lower surface of the support member by a flexible hinge attachment. The support member preferably includes ring engaging means for releasably engaging the support ring such that the support ring is engageable in the support member such that a bottom surface of the support ring is flush with the lower surface of the support member. The support ring is preferably attached to the support member just in front of the interface between the front two-thirds and the rear one-third. Therefore, when the support ring is disengaged, and the drainage bag is attached or hung on the support ring, the weight of the drainage bag adds to the torsion load urging the front two-thirds downward. This adds further stability to the fit between the carrying device and the cross-braces.

Preferably, the catheter tube engaging means includes a plurality of clip members attached to the upper surface of the support member. The excess catheter tubing is engageable in the clip members so that the excess tubing is oriented substantially in the same orientation as the upper surface. When the support member is attached to the wheelchair such that the upper surface is in a substantially horizontal orientation, the excess catheter tubing engaged in the clip members is oriented in a substantially horizontal orientation. Preferably, the clip members are pop-out compression clips and preferably the plurality of clip members include four clip members attached to the upper surface of the support member so as to radiate substantially around a center of the upper surface such that the excess catheter tubing can be looped substantially around the center when it is received in the clip members.

The present invention also provides a method of maintaining a gravity flow drainage system for indwelling urinary catheter. The drainage system includes a flexible catheter drainage tube and a drainage bag. The drainage tube connects the catheter to the drainage bag so that fluid can pass from the catheter to the drainage bag through the tube. The drainage system includes excess catheter tubing when an entire length of the drainage tube is not needed to span a distance of a direct, passable, decending pathway between the catheter and the drainage bag. The method comprises engaging excess catheter tubing in catheter tube support means for engaging excess catheter tubing. The support means include retention means for retaining excess catheter tubing in a substantially horizontal orientation such that the catheter drainage tube contains no vertical loops which interfere with the maintenance of the gravity flow drainage system.

Furthermore, the present invention preferably provides a method of maintaining a gravity flow drainage system so that urine will pass from an indwelling urinary catheter through the flexible catheter drainage tube and into the drainage bag without collecting in low spots in the drainage tube. The device provided by the present invention will greatly reduce the risk that bacteria will multiply in low spots in the drainage tube so as to provide a potential for urinary passage contamination or infection as often occur when such a device is not available. The present invention provides straight forward methods for collecting excess catheter tubing when the excess tubing is not required to span the distance between the catheter and the drainage bag. The excess tubing is collected in such a manner that there are no vertical loops in the tube which would otherwise allow urine to collect. Because the excess tubing is collected in this manner, the urine is allowed to flow at the urging of the force of gravity through the catheter drainage tube to the drainage bag without collecting in the drainage tube. Therefore, the present invention can be used to reduce the risk of infection to the catheterized patient or nursing home resident by reducing the potential for collection of urine in a gravity flow drainage system which would provide a medium for bacterial growth at a point closer to the urinary passageway than would otherwise be present.

In addition, the invention securely attaches the drainage bag to the wheelchair at an acceptable level wherein the bag will not drag on the floor and fall off the wheelchair. Therefore, the present invention also reduces the risk of infection by minimizing external bacterial contamination of the bag and tubing caused by contact with the floor or other unsanitary surfaces.

In preferred embodiments of the present invention a device is provided which allows hospital and nursing home aides to easily engage and disengage excess catheter tubing in the device and to attach and detach the device to a wheelchair in a position below the seat of the wheelchair. The device is inconspicuous and out of the way when it is in this position. The drainage bag is protected from colliding with stationary objects by the frame of wheelchair as the wheelchair is moved from place to place and the drainage bag is partially removed from the view of people standing near the wheelchair when the drainage bag is attached to the device because of its location below the seat of the wheelchair. The present invention supports both the excess catheter tubing and the drainage bag so that they do not touch the ground or brush against passing objects when the wheelchair is moved thus reducing the potential for external contamination. The device offers patients/residents increased privacy because the device is placed under the seat of the wheelchair and is not, therefore, seen by the patient/resident or by most people who are nearby.

In the context of the present application the following terms have the following meanings. A "loop" in a tube or tubing is a turn or a change in direction in the tube or tubing wherein the tube or tubing turns or changes direction such that it substantially returns in the same general direction from whence it came or such that fluid passing through the loop in the tube or tubing must travel a distance in one general direction and then return from the farthest point reached in that direction. A "vertical loop" is a loop which extends substantially in a downward direction and returns therefrom creating a low point in the loop which is the point in the loop which has the lowest relative elevation. A loop has a "substantially horizontal orientation" when the loop in the tube or tubing is substantially level, or when the tube or tubing in the loop remains substantially within the same or similar horizontal plane, or when the lowest spot in the loop, or in the tube or tubing in the loop, is not sufficiently low to allow fluid to collect to a sufficient degree in the low spot that fluid can fill in the entire cross section of the tube or tubing at the lowest point in the low spot without flowing out of the low spot into other sections of the tube or tubing. A loop which "radiates substantially around", or "loops substantially around", a center of the upper surface of the support member turns or changes direction such that it has a rounded or elliptical path between some points around the center of the surface, but does not indicate that the loop is a complete loop, circle or ellipse. A surface ma be "flush" with another surface when the two surfaces are substantially in the same place. A "passable" pathway is a pathway which is passable without putting the object to pass through this pathway through any existing or previous non-existing enclosures, recesses, openings, holes or breaks in the structure or matter comprising the wheelchair or a person sitting in the wheelchair or a person sitting in the wheelchair. A "direct" pathway is a pathway which is a substantially direct pathway given the other requirements which the pathway must meet. A "descending" pathway is a pathway which descends substantially along its length although it may have some small percentage of areas along its length which do not descend but do not create vertical loops and or significant areas which remain in a substantially horizontal orientation. "Span" means to extend from one point along a path to another point along a path. The "front two-thirds" of the carry device is a portion of the device which comprises about two-thirds of the horizontal cross-sectional area of the device nearest the front of a wheelchair when properly attached to the wheelchair such that a larger portion of the device is located in front of the cross-braces. In this context, about two-thirds means more than one-half. The "rear one-third" of the carrying device is a portion of the device which comprises about one-third of the horizontal cross-sectional area of the device nearest the rear of the wheelchair such that the larger portion of the device is located in front of the cross-braces. In this context, one-third means less than one-half. An "interface" between the front two-thirds and the rear one-third exists at a horizontal line through a vertical plane which exists between the two cross-braces to which the preferred carry device is properly attached. A "torsion load" is a load on an end of a device, preferably on the front two-thirds of the present device, which causes the end to have a downward pressure on it so that the end will be urged to turn or twist along an axis line, preferably proximate the interface between the front two-thirds and the rear two thirds.

The above described features and advantages along with various other advantages and features of novelty are pointed out with particularity in the claims of the present application. However, for a better understanding of the invention, its advantages, and objects attained by its use, reference should be made to the drawings which form a further part of the present application and to the accompanying descriptive matter in which there is illustrated and described preferred embodiments of the present invention.

BRIEF DESCRIPTION OF THE DRAWINGS

In the drawings, in which like reference numerals and letters indicate corresponding parts throughout the several views.

FIG. 2 is a perspective view of a catheter drainage tube engaged to an embodiment of the catheter tube carrying device of the present invention;

FIG. 3 is a plan view of the upper surface of the catheter tube carrying device shown in FIG. 2;

FIG. 4 is a plan view of the lower surface of the catheter tube carrying device shown in FIGS. 2 and 3;

FIG. 5 is a cross-sectional side view along line 5—5 as shown in FIG. 3;

FIG. 6 is a sectional view of the pop-down drainage bag support ring of the catheter carrying device shown in FIGS. 2–5 which is engaged in the support member and disengaged in phantom;

FIG. 7 is a perspective view of an alternate embodiment of the catheter tube carrying device; and FIG. 8 is a perspective view of a flexible catheter drainage tube collected in vertical loops and attached to a wheelchair as it may have been collected and attached according to prior art methods prior to any use of the present invention.

DETAILED DESCRIPTION OF PREFERRED EMBODIMENTS OF THE PRESENT INVENTION

Figure 1:
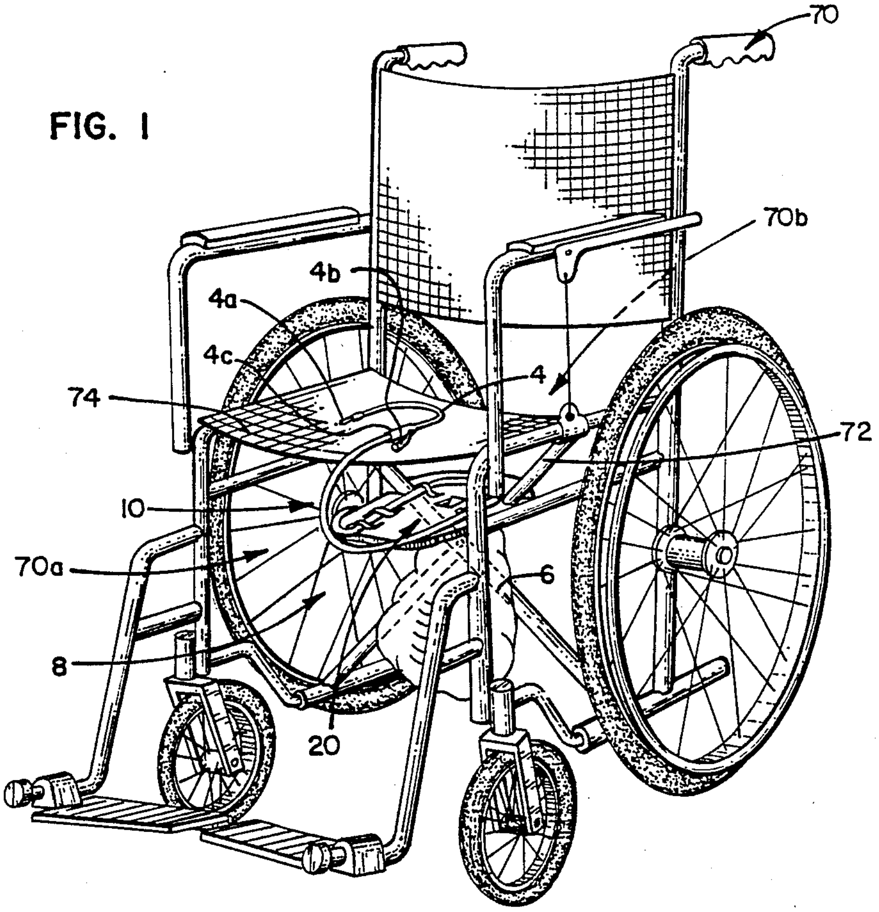
FIG. 1 is a perspective view of a gravity flow drainage system supported by a catheter tube carrying device which is attached to a wheel chair.

Referring to the drawings and initially to FIG. 1, the reference numeral 10 refers to a flexible catheter drainage tube which is engaged in a catheter tube carrying device 20. The catheter tube carrying device 20 is attached to a wheelchair 70 having a front **70*a* and a rear 70*b*. The catheter drainage tube 10 is attached to an indwelling urinary catheter 4** which is normally inserted in a person's urinary passageway in order to catheterize a person who is incontinent.

A "Foley" catheter 4 is shown in FIG. 1. The "Foley" catheter 4 has a tip **4*a*, a tip inflation inlet member 4*b* located just above a catheter base 4*c* which is connected to an upper end 10*a* of the flexible catheter drainage tube 10. The tip 4*a* of the "Foley" catheter 4 is inserted through a person's urethra and into the bladder using standard sterile techniques. When the tip 4*a* is in the bladder it is inflated by infusing air, water, or the like into the tip 4*a* by means of the tip inflation inlet member 4*b*. Once the tip 4*a* is slightly inflated it will remain in the bladder because it is too large to slide easily back through the urethra. It will be appreciated that the degree to which the tip 4*a* must be inflated will cary slightly as the idiosyncrasies of each person to be catheterized require. A lower end 10*b* of the drainage tube 10 runs into, and preferably connects the tube 10 to the drainage bag 6**.

When the catheterized person is sitting in a wheel chair 70, the tip **4*a* of the indwelling catheter 4 is positioned in the urinary passageway and the rest of the catheter 4 generally extends down between the length of the person's legs. The catheter drainage tube 10 is connected to the base 4*c* of catheter 4, generally runs away from the indwelling catheter 4, and connects the catheter 4 to a drainage bag 6. The catheter tube 10 provides a passageway for fluid flowing out of the catheter 4 and into the drainage bag 6 thereby creating a gravity flow drainage system 8 which includes the tube 10 and the bag 6. Preferably, the system 8 provides an environment which is closed to the exterior and connected only to the catheter whose open end near the tip 4*a* is the only opening to the exterior of the otherwise closed environment. When the fluid, preferably urine, flows from the catheter 4 to the drainage bag under the force of gravity without interruption, a working gravity flow drainage system 8** exists.

Referring now to FIGS. 2–5, a working gravity flow drainage system 8 can be maintained when the length of the flexible catheter drainage tube 10 is greater than the length required to span a distance of a direct, passable, decending pathway between an indwelling urinary catheter 4 positioned appropriately in a urinary passageway of a person when the person is sitting in the seat 74 of the wheelchair 70 and the drainage bag 6 when the drainage bag 6 is located at an elevation lower than the elevation of the seat 74 of the wheelchair 70. To maintain such a system 8, excess catheter tubing 12, which is a portion of the flexible catheter drainage tube 10 which is not required to span the distance of said direct, passable, descending pathway, may be engaged in a catheter tube carrying device 20 of the present invention so that a loop or loops in the excess catheter tubing 12 are oriented in a substantially horizontal orientation. When the excess catheter tubing 12 is engaged in the catheter tube carrying device 20 and the carrying device 20 is attached to the wheelchair 70 in such a manner that the upper surface 22 of the carrying device 20 is oriented in a substantially horizontal orientation as is shown in FIGS. 1, 2 and 5.

The carrying device 20 of the preferred embodiment shown in FIGS. 1–6 includes a support member 21 having upper and lower surfaces 22 and 24, a plurality of clip members, preferably pop-out compression clips 26 for engaging excess catheter tubing 12, and a plurality of recesses, preferably slip fit recesses 30 for attaching the support member 21 to the wheelchair 70. The excess catheter tubing 12 is engaged in the plurality of clips 26 which are attached to the upper surface 22 of the support member 21 by popping the clips 26 up from a first stable position as shown in FIGS. 2–5, to a second, open, position which allows the tube 10 to be easily engaged therein. The clips 26 are then snapped closed to engage and support the tube 10 while occupying the first stable position. The clips 26 provide a mechanism for engaging excess catheter tubing 12 and for supporting and receiving the catheter drainage tube 10. These clips 26 are arranged to substantially radiate around a center 28 of the upper surface 22 of the support member 21 so that the excess catheter tubing 12 loops substantially around the center 28 of the upper surface 22 when the excess catheter tubing 12 is engaged in the clips 26. When the catheter tube carrying device 20 is attached to the wheelchair 70 so that the upper surface 22 of the support member 21 is oriented in a substantially horizontal orientation, the excess catheter tubing 12 engaged in the clips 26 is oriented in a substantially horizontal orientation.

The preferred embodiment of the catheter tube carrying device 20 of the present invention includes slip fit recesses 30 which receive cross-braces 72 which provide support for the wheelchair 70. The cross-braces 72 are located below the seat 74 of the wheelchair 70. The catheter tube carrying device 20 can be attached to the wheelchair 70 by engaging the cross-braces 72 in the slip fit recesses 30 located on either side of the catheter tube carrying device 20, as shown in FIGS. 2–5. If the catheter tube carrying device 20 is properly positioned above an intersection 76 of the cross-braces 72 held together by a bolt 78, the location of the carrying device 20 will provide room for the drainage bag 6 so that the drainage bag 6 may be attached to the carrying device 20 and not touch the ground. Proper positioning of the carrying device 20 on the cross-braces 72 allows the carrying device 20 to be oriented such that the upper surface 22 of the support member 21 is oriented in a substantially horizontal orientation. This allows the excess catheter tubing 12 engaged in the clips 26 to be oriented in a substantially horizontal orientation so as to reduce the tendency for fluid to collect in low points in the flexible catheter drainage tube 10.

Now referring also to FIG. 6, the preferred embodiment shown in FIGS. 1–6 includes a pop-down support ring 40 which is attached to the lower surface 24 of the support member 21. The support ring 40 is attached to the lower surface 24 by means of a flexible hinge attachment 42 which allows the support ring 40 to bend at the attachment 42 so as to allow the front end 44 of the support ring 40 to pop out of the support member 21 when urged to do so by pulling on the support ring 40. The support ring includes an opening 46 which can receive a drainage bag hook 7 or other well known attaching or binding mechanism, such as other types of hooks, straps, strings, and the like, for attaching the drainage bag 6 to the support ring 40. When the support ring 40 is pushed into the support member 21 so that a bottom surface 48 of the support ring 40 is flush with the lower surface 24 of the support member 21, the front end 44 of the support ring 40 is engaged in the support member 21 by the front edge 50 of the support ring recess 52 such that there is an interference fit between the front edge 50 and the front end 44.

FIGS. 2–5 show the preferred catheter tube carrying device 20 attached to the cross-braces 72 shown in phantom in FIGS. 2, 3, and 5. The carrying device 20 has a front two-thirds **20*a* and a rear one-third 20*b* which are separated by an interface 23 proximate to a vertical plane 25 passing between the cross-braces 72 when the device 20 is properly attached to the wheelchair 20 as illustrated in FIGS. 2, 3 and 5. The inner surface 32 of each slip fit recess 30 is sized such that when the cross-braces 72 are received in the recesses 30, they contact the inner surfaces 32. Because the front two-thirds 20*a* weighs more than the rear one-third 20*b*, the carrying device 20 is cantilevered at the point of contact between the device 20 and the wheel-chair 70. A load is provided by the excess weight of the front two-thirds 20*a* over the weight of the rear one-third 20*b*, such that the cross-braces 72 and the inner surfaces 32 provide a torsion loaded fit which enables the recesses 30 to firmly engage the cross-braces 72. This limits or prevents slippage of the carrying device 20 with respect to the cross-braces 72, and consequential changes in the orientation of the support member 21 or the catheter carrying device 20 with respect to the horizontal orientation which is preferred. This can be especially important when the wheelchair 70 is moved, or when the wheelchair 70 bumps into objects which may be in its path. When the wheelchair 70 has such a collision, the collision may jar the catheter tube carrying device 20. However, the torsion loaded fit reduces the tendency of the device 20 to become disengaged from the cross-braces 72 or from slipping along the cross-braces 72, thereby allowing the orientation of the upper surface 22 of the support member 21** to change.

An alternate embodiment of the catheter carrying device 20′ is shown in FIG. 7 engaged to sections of cross-braces 72′ which are shown in phantom. The catheter carrying device 20′ includes a support member 21′, cross-brace engaging members 34′ which are slightly offset to accommodate the cross-braces 72′, and catheter tube receiving clips 26′ for supporting and engaging the catheter tube 10′ and collecting excess catheter tubing 12′. A drainage bag support ring 40′ is shown in phantom attached to the lower surface 24′ of the support member 21′.

A catheter tube 10″ is shown in FIG. 8 as it may have been gathered prior to the Applicants present invention. When excess catheter tubing 12″ is gathered and attached to the side of a wheelchair 70″, it can be looped around several times such that vertical loops 13 are formed which have low spots 14. Even if the drainage bag 6" is attached to the wheelchair 70" at an elevation which is lower than the elevation of the seat 74" in which the patient/resident who is catheterized will sit, the urine passing through the catheter tube 10" will not pass all the way to the drainage bag 6" because it will collect in the low points 14 in the vertical loops 13 and interrupt the gravity flow drainage system 8" which includes the tube 10" and the bag 6", and would be connected to an indwelling urinary catheter 4" (not shown here). As discussed hereinabove, this presents serious potential for contamination when the system 8" is connected and in use.

The gravity flow drainage system 8 for an indwelling urinary catheter 4 may be maintained by retaining excess catheter tubing 12 in a substantially horizontal orientation at an elevation lower than the elevation of the urinary catheter 4 such that a loop or loops in the drainage tube 10 are retained in a substantially horizontal orientation such that liquid does not collect in the loop or loops in sufficient quantities to restrain fluid passage from the catheter 4 to the drainage bag 6 through the tube 10. Preferably, the drainage bag 6 is supported at an elevation lower than the elevation of the excess catheter tubing 12 so that liquid in the drainage tube 10 is urged to drain into the drainage bag 6 by the force of gravity. The gravity flow drainage system 8 may be maintained by retaining excess catheter tubing 12 in a horizontal orientation such that liquid does not collect in low spots in loops in the catheter drainage tube, thereby interrupting the gravity flow drainage system 8. Preferably, the gravity flow drainage system 8 for the indwelling urinary catheter 4 is maintained by a method comprising engaging excess catheter tubing 12 in a catheter tube carrying device 20 wherein any loop in the excess catheter tubing 12 is retained in a substantially horizontal orientation when the upper surface 22 of the support member 21 is oriented in a substantially horizontal orientation. This may be accomplished by engaging the catheter tube carrying device 20 on the cross-braces 72 below the seat 74 of the wheelchair 70 in such a way as to orient the upper surface 22 of the support member 21 in a substantially horizontal orientation. Further positioning the drainage bag 6 at an elevation less than the elevation of the drainage tube 12 is preferred. Preferably, the drainage bag 6 is attached to the catheter tube carrying device 20 such that the drainage bag 6 is located at an elevation lower than the elevation of the excess drainage tubing 12 engaged in the carrying device 20.

While certain representative embodiments of the present invention have been described herein for the purposes of illustration, it will be apparent to those skilled in the art that modifications therein may be made without departing from the spirit and scope of the present invention.

What is claimed is:

1. A catheter tube carrying device for use in conjunction with the use of a wheelchair by a person who must be catheterized, the wheelchair having lateral sides, a seat and cross-braces located below the seat connecting the lateral sides, each of said lateral sides having at least one wheel in its vertical plane, said catheter tube carrying device comprising catheter tube support means for engaging catheter tubing of a gravity flow drainage system for an indwelling urinary catheter, the gravity flow drainage system including a flexible catheter drainage tube including catheter tubing and a drainage bag, the drainage tube connecting the catheter to the drainage bag such that fluid can pass from the catheter to the drainage bag through the tube, said catheter tube support means including means for horizontally engaging the cross-braces in a location below the seat, wherein a portion of the catheter tubing is engageable in said catheter tube support means such that said portion of catheter tubing retained by said catheter tube support means can be retained in such a position that said retained tubing provides a substantially horizontal or a descending pathway for fluid which passes through the catheter tubing to the drainage bag from the catheter.

2. The catheter tube carrying device of claim 1 wherein said carrying device comprises drainage bag support means for supporting the drainage bag at an elevation lower than the elevation of said portion of catheter tubing received by said catheter tube support means.

3. A catheter tube carrying device for attachment to a wheelchair, the wheelchair having lateral sides, a seat and cross-braces located below the seat connecting the lateral sides, each of said lateral sides including at least one wheel in its lateral plane, said catheter tube carrying device comprising a support member, said support member including wheelchair attaching means for attaching said support member to the wheelchair below the seat, said support member including catheter tube support means for engaging catheter tubing of a gravity flow drainage system for an indwelling urinary catheter, the gravity flow drainage system including a flexible drainage tube including catheter tubing and a drainage bag such that fluids can pass from the catheter to the drainage bag through the tube, wherein said support member is attachable to the wheelchair in a substantially horizontal position below the seat such that catheter tubing received by said catheter tube support means can be retained in a substantially horizontal orientation, wherein said attaching means include cross-brace receiving means for receiving the cross-braces such that said carrying device can be horizontally attached to the wheelchair by engaging the cross-braces in said cross-brace receiving means.

4. The catheter tube carrying device of claim 3 wherein said support member includes drainage bag support means for supporting the drainage bag at an elevation lower than an elevation of a portion of catheter tubing received by said catheter tube support means.

5. The catheter tube carrying device of claim 3, said cross-brace receiving means including slip fit recess means for engaging the cross-braces, said recess means including a plurality of slip fit recesses, each of said recesses having inner surfaces which contact the respective cross-brace, wherein the carry device engages the cross-braces in a torsion loaded fit which resists slippage along the cross-braces when the cross-braces are engaged in said recesses.

6. The catheter tube carrying device of claim 3, wherein said support member includes upper and lower surfaces and a pop-down drainage bag support ring attached to said lower surface by a flexible hinge attachment, said support member including ring engaging means for releasably engaging said support ring such that the support ring is engageable in said support member such that a bottom surface of said support ring is flush with said lower surface of said support member.

7. The catheter tube carrying device of claim 3, said support member having upper and lower surfaces, said support member including a plurality of clip members attached to said upper surface, a portion of catheter tubing being engageable in said clip members such that said portion of tubing can be oriented in substantially the same orientation as said upper surface, wherein the support member is attachable to the wheelchair such that the upper surface is in a substantially horizontal orientation and such that the portion of catheter tubing so engaged in said clip members can be oriented in a substantially horizontal orientation.

8. The catheter tube carrying device of claim 7, said clip members being pop-out compression clips.

9. The catheter tube carrying device of claim 7, said plurality of clip members including four clip members attached to said upper surface so as to radiate substantially around a center of said upper surface such that said catheter tubing can be looped substantially around said center when said tubing is received in said clip members.

10. A catheter tube carrying device for attachment to a wheelchair having a seat, the carrying device comprising;

(a) a support member having upper and lower planar surfaces, said upper surface for supporting a catheter tube;

(b) said support member having wheelchair attaching means;

(c) said wheelchair attaching means for attaching said support member to the wheelchair, said attaching means removably attaching and securing said support member to the wheelchair in a substantially horizontal plane below the seat, and (d) catheter tube receiving means on said upper surface of said support member for receiving a portion of catheter tubing, said receiving means to receive and hold said portion of catheter tubing in a substantially horizontal orientation when said support member is attached to the wheelchair such that said upper surface is orientated in a generally horizontal orientation.

11. The catheter tube carrying device of claim 10, including drainage bag support means for supporting a catheter drainage bag attached to the catheter tube.

12. The catheter tube carrying device of claim 10, wherein said catheter tube receiving means include a plurality of clip members, the catheter tubing being engageable in said clip members.

13. The catheter tube carrying device of claim 12, wherein said catheter tube receiving means include a plurality of clip members attached to said upper surface, said plurality of clip members arranges substantially around a center of the upper surface such that said catheter tubing can be looped substantially around the center of the upper surface when a portion of said catheter tubing is engaged in said plurality of clips.

14. A method of maintaining a gravity flow drainage system for an indwelling urinary catheter in fluid communication with a fluid transmitting organ of a person sitting in a seat of a wheelchair, the wheelchair having lateral sides and cross-braces located below the seat connecting the lateral sides, each of said sides including at least one wheel in its lateral plane, the drainage system including a drainage bag and a flexible catheter tube connecting the urinary catheter to the drainage bag such that fluid can pass from the catheter to the drainage bag through the tube, the drainage system including excess catheter tubing when an entire length of the drainage tube is in excess of that requires to span a distance of a direct, passable descending pathway between the catheter and the drainage bag, said method comprising the steps of:

(a) providing a catheter tube carrying device including catheter tube support means for engaging excess catheter tubing, upper and lower surfaces and wheelchair engaging means for horizontally attaching said carrying device to the cross-braces below the seat of the wheelchair;

(b) engaging a portion of excess catheter tubing with said catheter tube support means; and (c) attaching said carrying device to the cross-braces such that said carrying device is located below the seat of the wheelchair and such that the upper surface of said carrying means is oriented in a substantially horizontal orientation.

15. The method of claim 14, wherein said carrying device includes drainage bag support means for supporting the drainage bag such that the drainage bag is located at an elevation lower than the elevation of excess catheter tubing engaged in said catheter tube support means, said method further comprising the step of attaching the drainage bag to said drainage support means.

* * * * *